(12) United States Patent
Kuchimaru et al.

(10) Patent No.: US 10,962,763 B2
(45) Date of Patent: Mar. 30, 2021

(54) OPTICAL UNIT

(71) Applicant: OLYMPUS CORPORATION, Tokyo (JP)

(72) Inventors: Toru Kuchimaru, Hachioji (JP); Yukiharu Makino, Hachioji (JP); Kazuhiko Hino, Hachioji (JP); Masahiro Maeda, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/694,099

(22) Filed: Nov. 25, 2019

(65) Prior Publication Data

US 2020/0166741 A1 May 28, 2020

Related U.S. Application Data

(63) Continuation of application No. PCT/JP2018/007867, filed on Mar. 1, 2018.

(30) Foreign Application Priority Data

May 26, 2017 (JP) .............................. JP2017-104400

(51) Int. Cl.
G02B 23/24 (2006.01)
G03B 17/12 (2021.01)

(52) U.S. Cl.
CPC ......... *G02B 23/2484* (2013.01); *G03B 17/12* (2013.01)

(58) Field of Classification Search
None
See application file for complete search history.

(56) References Cited

U.S. PATENT DOCUMENTS 4,323,304 A * 4/1982 Ishii .................... A61B 1/00126
396/17
5,894,369 A 4/1999 Akiba et al.
(Continued)

FOREIGN PATENT DOCUMENTS

EP  2 605 053 A1  6/2013
JP  10-151106 A   6/1998
(Continued)

OTHER PUBLICATIONS

International Search Report dated Jun. 5, 2018 received in PCT/JP2018/007867.

*Primary Examiner* — William B Perkey
(74) *Attorney, Agent, or Firm* — Scully, Scott, Murphy Presser, P.C.

(57) ABSTRACT

An optical unit includes: an objective lens unit arranged on a distal end side; an image pickup unit arranged on a proximal end side of the objective lens unit; an optical frame; an image pickup device frame; a proximal-end-side outer circumferential face provided on a proximal end side of the optical frame; an inner circumferential face of a distal-end-side frame body provided on a distal end side of the image pickup device frame; a plurality of notches provided apart in a circumferential direction on an outer circumferential face of one of the frames, the plurality of notches having opening portions on end faces where the optical frame and the image pickup device frame face each other; and holding portions provided on an outer circumferential face of the other frame different from the one frame, the holding portions passing through the opening portions and being accommodated in the notches.

9 Claims, 10 Drawing Sheets

(56) References Cited

U.S. PATENT DOCUMENTS

| | | | |
|---|---|---|---|
| 2005/0050707 A1* | 3/2005 | Scott | B25B 9/02 29/426.5 |
| 2005/0104995 A1* | 5/2005 | Spryshak | G03B 17/12 348/360 |
| 2008/0130135 A1* | 6/2008 | Shigetoshi | H04N 5/2254 359/701 |
| 2011/0075276 A1* | 3/2011 | Lin | G02B 7/021 359/819 |
| 2011/0242409 A1* | 10/2011 | Hsieh | G03B 17/12 348/374 |
| 2013/0027534 A1 | 1/2013 | Kibayashi | |
| 2013/0201566 A1* | 8/2013 | Wu | G02B 7/10 359/704 |
| 2016/0166132 A1* | 6/2016 | Sasamoto | A61B 1/0008 600/109 |
| 2016/0302647 A1* | 10/2016 | Orihara | G02B 23/2484 |
| 2017/0230550 A1* | 8/2017 | Leong | H04N 5/2254 |
| 2018/0364441 A1* | 12/2018 | Hubert | H04N 5/23287 |
| 2019/0335068 A1* | 10/2019 | Kato | G02B 23/2484 |
| 2019/0357760 A1* | 11/2019 | Nara | A61B 1/00124 |
| 2020/0064618 A1* | 2/2020 | Kuchimaru | H04N 5/2254 |
| 2020/0166741 A1* | 5/2020 | Kuchimaru | G03B 15/00 |

FOREIGN PATENT DOCUMENTS

| | | |
|---|---|---|
| JP | 2002-095626 A | 4/2002 |
| JP | 2003-102681 A | 4/2003 |
| JP | 2007-041141 A | 2/2007 |
| JP | 2015-062555 A | 4/2015 |
| WO | 2012-137739 A1 | 10/2012 |

* cited by examiner

US 10,962,763 B2

OPTICAL UNIT

CROSS REFERENCE TO RELATED APPLICATION

This application is a continuation application of PCT/JP2018/007867 filed on Mar. 1, 2018 and claims benefit of Japanese Application No. 2017-104400 filed in Japan on May 26, 2017, the entire contents of which are incorporated herein by this reference.

BACKGROUND OF THE INVENTION

1. Field of the Invention

The present invention the present invention relates to an optical unit configured by assembling a lens frame and an image pickup device frame together.

2. Description of the Related Art

Recently, endoscopes have been used in a medical field, an industrial field and the like. Among the endoscopes, there are so-called electronic endoscopes with a solid-state image pickup device, such as a CCD, disposed on a distal end portion of an insertion portion. In the electronic endoscopes, an optical image formed on an image pickup surface of the CCD is displayed on a screen of a display device so that observation can be performed.

Japanese Patent Application Laid-Open Publication No. 2003-102681 discloses an electronic endoscope with an image pickup unit built in a distal end portion of the endoscope. The image pickup unit is configured with an objective optical system to be an objective lens with a plurality of optical members disposed in a lens frame, and an image pickup portion with an image pickup surface of a solid-state image pickup device arranged at an image formation position of the objective optical system. A centering lens and a mask member are arranged on a front face of the solid-state image pickup device, and the centering lens is integrally fixed to a device frame by bonding fixation. The lens frame and the device frame are integrally fixed, for example, by adhesive after focus adjustment is performed.

Recently, a high accuracy has been required for assembly between a lens frame and an image pickup device frame accompanying narrowing of a pitch of an image pickup device. Therefore, focus adjustment between a lens frame and an image pickup frame, that is, position adjustment in an optical axis direction is performed by changing a mating length between the lens frame and the image pickup device frame.

As shown in FIGS. 1A and 1B, in a configuration in which a mating length L1 between a lens frame 1 and an image pickup device frame 2 is sufficiently secured, for example, an area of a lens-side jig grasping face 1*a* provided on the lens frame 1 is extremely small in comparison with an area of a device-side jig grasping face 2*a* provided on the image pickup device frame 2.

In comparison, for example, when an area of a lens-side jig grasping face 4*a* provided on a lens frame 4 and an area of a device-side jig grasping face 5*a* provided on an image pickup device frame 5 are made almost equal as shown in FIGS. 2A and 2B, grasping of the frames 4 and 5 by a jig 3 can be certainly performed.

SUMMARY OF THE INVENTION

An optical unit of an aspect of the present invention is provided with: a first optical system arranged on a distal end side; a second optical system that is coaxial with the first optical system and is arranged on a proximal end side of the first optical system; a first holding frame in which the first optical system is provided; a second holding frame in which the second optical system is provided; a first mating face provided on a proximal end side of the first holding frame and forming an outer circumferential face, the first mating face constituting a mated portion between the first holding frame and the second holding frame; a second mating face provided on an inner circumferential face on a distal end side of the second holding frame, the second mating face being arranged mating with the first mating face; a plurality of accommodating recess portions provided apart in a circumferential direction on an outer circumferential face of one of the first holding frame and the second holding frame, the plurality of accommodating recess portions having openings on end face sides where the first holding frame and the second holding frame face each other and being formed along the optical axis; and a plurality of nail members provided on an outer circumferential face of another holding frame different from the one holding frame, between the first holding frame and the second frame, the plurality of nail members passing through the openings and being accommodated into the accommodating recess portions, wherein in a state in which the nail members are stored in the accommodating recess portions, bottom faces of the accommodating recess portions and mating faces of the nail members are in a mated state, and recess portions forming gaps are provided on a distal end sides of the nail members.

An optical unit of another aspect of the present invention is provided with: a first optical system; a second optical system arranged coaxially with the first optical system; a first holding frame in which the first optical system is provided; a second holding frame in which the second optical system is provided, the second holding frame mating with the first holding frame; a first mating face provided on the first holding frame and forming an outer circumferential face, the first mating face constituting a mated portion between the first holding frame and the second holding frame; a second mating face provided on an inner circumferential face of the second holding frame, the second mating face being arranged mating with the first mating face; a plurality of accommodating recess portions provided apart in a circumferential direction on an outer circumferential face of one of the first holding frame and the second holding frame, the plurality of accommodating recess portions having openings on end face sides where the first holding frame and the second holding frame face each other and being formed along the optical axis; and a plurality of nail members provided on an outer circumferential face of another holding frame different from the one holding frame, between the first holding frame and the second holding frame, the plurality of nail members passing through the openings and being accommodated into the accommodating recess portions, wherein, in a state in which the nail members are stored in the accommodating recess portions, bottom faces of the accommodating recess portions and mating faces of the nail members are in a mated state, and recess portions forming gaps are provided on distal end sides of the nail members.

DETAILED DESCRIPTION OF THE PREFERRED EMBODIMENTS

Figure 1A:
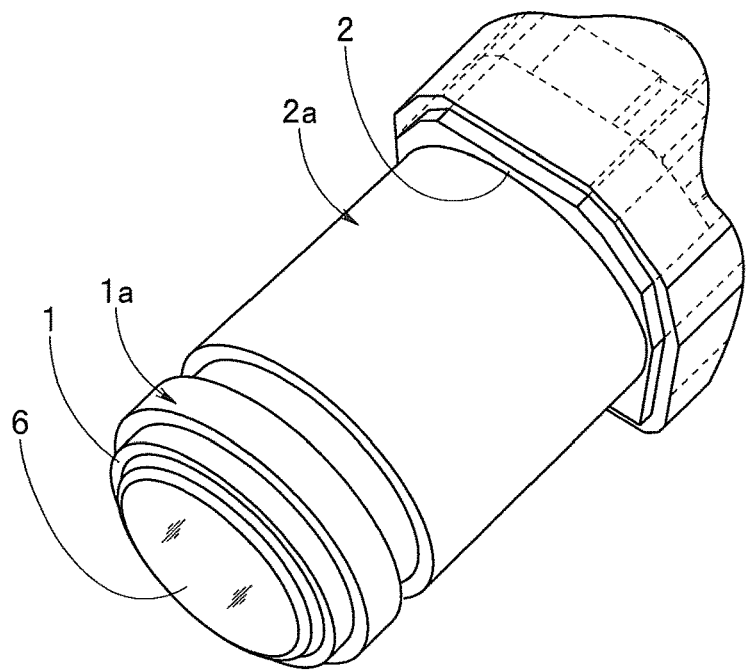
FIG. 1A is a diagram illustrating a configuration example of a lens frame and an image pickup device frame.
Figure 1B:
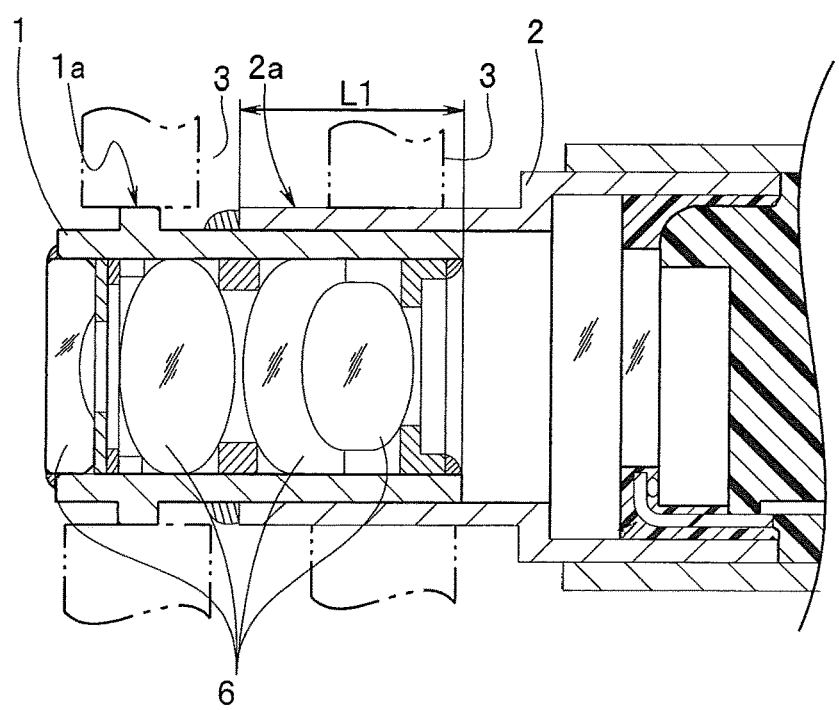
FIG. 1B is a longitudinal sectional view illustrating an optical unit of FIGS. 1A and 1*s* a diagram illustrating a problem caused by sufficiently securing a mating length between the lens frame and the image pickup device frame.
Figure 2A:
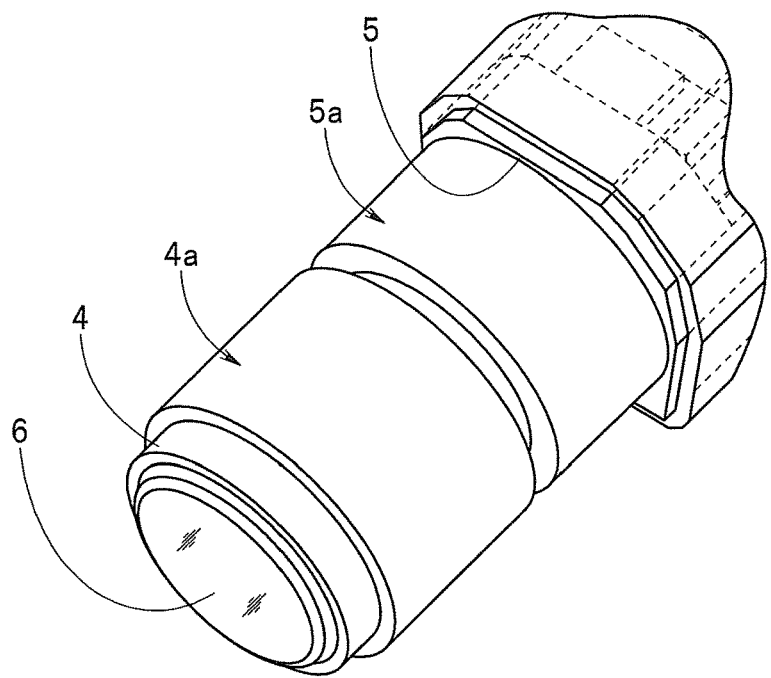
FIG. 2A is a diagram illustrating another configuration example of a lens frame and an image pickup device frame.
Figure 2B:
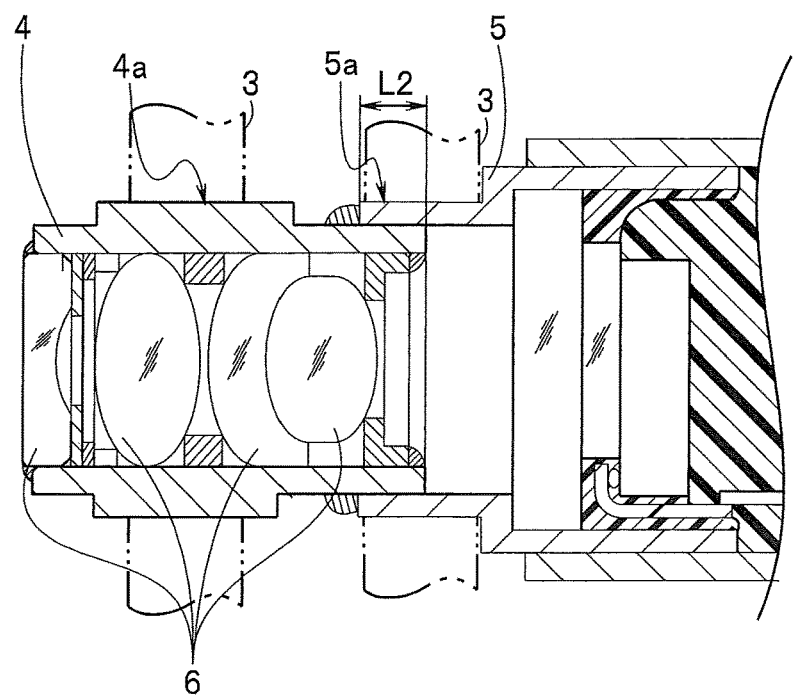
FIG. 2B is a longitudinal sectional view illustrating an optical unit of FIG. 2A and is a diagram illustrating a problem caused by making an area of a lens-side jig grasping face and an area of a device-side jig grasping face of the image pickup device frame equal.

Embodiments of the present invention will be described below with reference to drawings.

Note that, in each of drawings used in the description below, a scale may be different for each component so that the component is in a size recognizable on the drawing. In other words, the present invention is not limited only to the number of components, shapes of the components, a size ratio among the components, and a relative positional relationship among the respective components illustrated in the drawings.

Figure 3A:
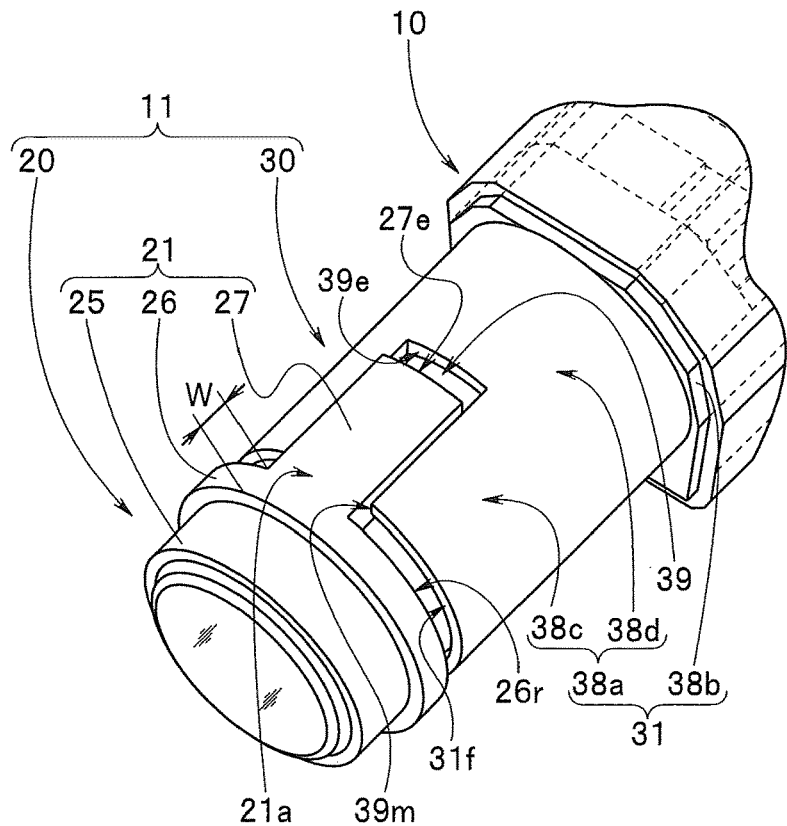
FIG. 3A is a diagram illustrating a configuration example of an optical unit of an image pickup apparatus.
Figure 3B:
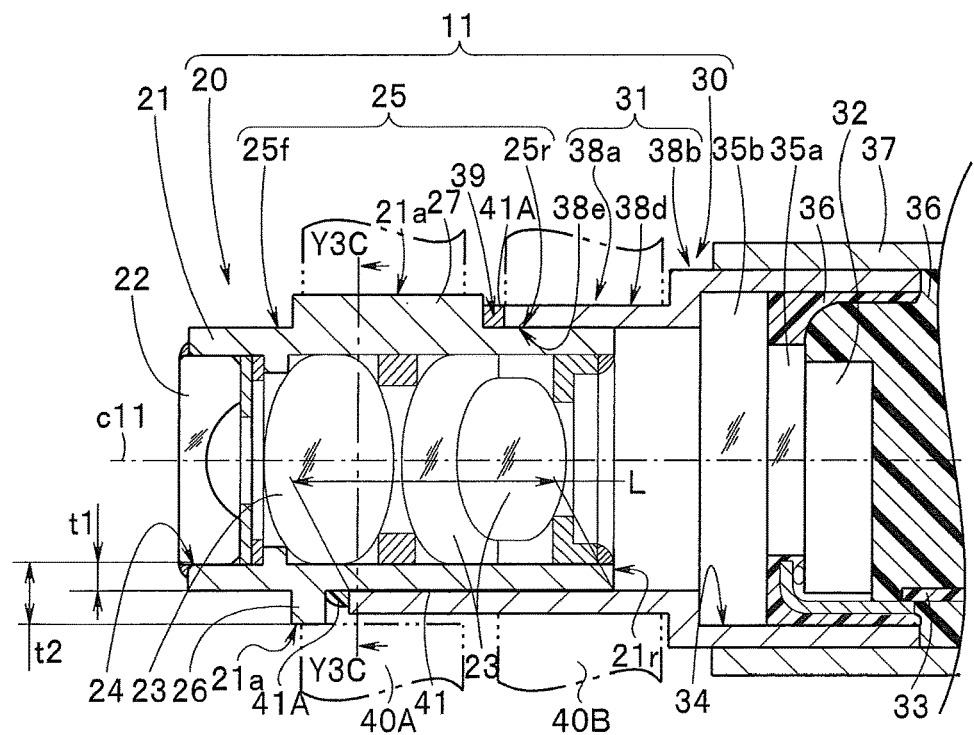
FIG. 3B is a longitudinal sectional view illustrating the optical unit of FIG. 3A and is a diagram illustrating a state in which, without increasing lengths of frame members, an optical frame of an objective lens unit further provided with an objective lens unit jig grasping face in addition to an outer circumferential face of a projecting portion and an image pickup device frame of an image pickup unit are integrally fixed.

As shown in FIGS. 3A and 3B, an optical unit 11 of an image pickup apparatus 10 is provided with an objective lens unit 20 which is a first optical system, and an image pickup unit 30 which is a second optical system. The objective lens unit 20 is arranged on a distal end side of the image pickup apparatus 10, and the image pickup unit 30 is arranged on a proximal end side of the objective lens unit 20.

As shown in FIG. 3B, the objective lens unit 20 is provided with an optical frame 21 which is a first holding frame, a distal end lens 22, a plurality of optical lenses 23, a filter which is an optical member, spacing rings and the like.

A first through hole 24 is formed in the optical frame 21 along a longitudinal axis (also referred to as an optical axis c11). In the first through hole 24, the distal end lens 22, the plurality of optical lenses 23, the filter, the spacing rings and the like which constitute the first optical system are held.

As shown in FIGS. 3A and 3B, the optical frame 21 is provided with a frame body 25 which is a first area and has a first outer diameter, and a projecting portion 26 and a holding portion 27, which constitute a second area and include a second outer diameter larger than the first outer diameter. The projecting portion 26 is an annular-shaped projecting portion with a width dimension of W, the projecting portion 26 projecting from an outer circumferential face of the frame body 25. An outer circumferential face of the projecting portion 26 constitutes a second area outer circumferential face 21a which can be at least an objective lens unit jig grasping face.

Note that the projecting portion 26 is an annular-shaped projecting portion in the present embodiment. However, the projecting portion 26 may be partially provided in a circumferential direction instead of being entirely circumferentially and seamlessly provided.

Reference symbol 25f in FIG. 3B indicates a distal-end-side outer circumferential face of the frame body 25 having a first thickness t1, the distal-end-side outer circumferential face being provided on a distal end side with respect to the projecting portion 26. Reference symbol 25r indicates a proximal-end-side outer circumferential face of the frame body 25, the proximal-end-side outer circumferential face being provided on a proximal end side with respect to the projecting portion 26. The proximal-end-side outer circumferential face 25r is a first mating face to mate with a distal-end-side inner circumferential face of an image pickup device frame (see reference symbol 31) described later.

Figure 3C:
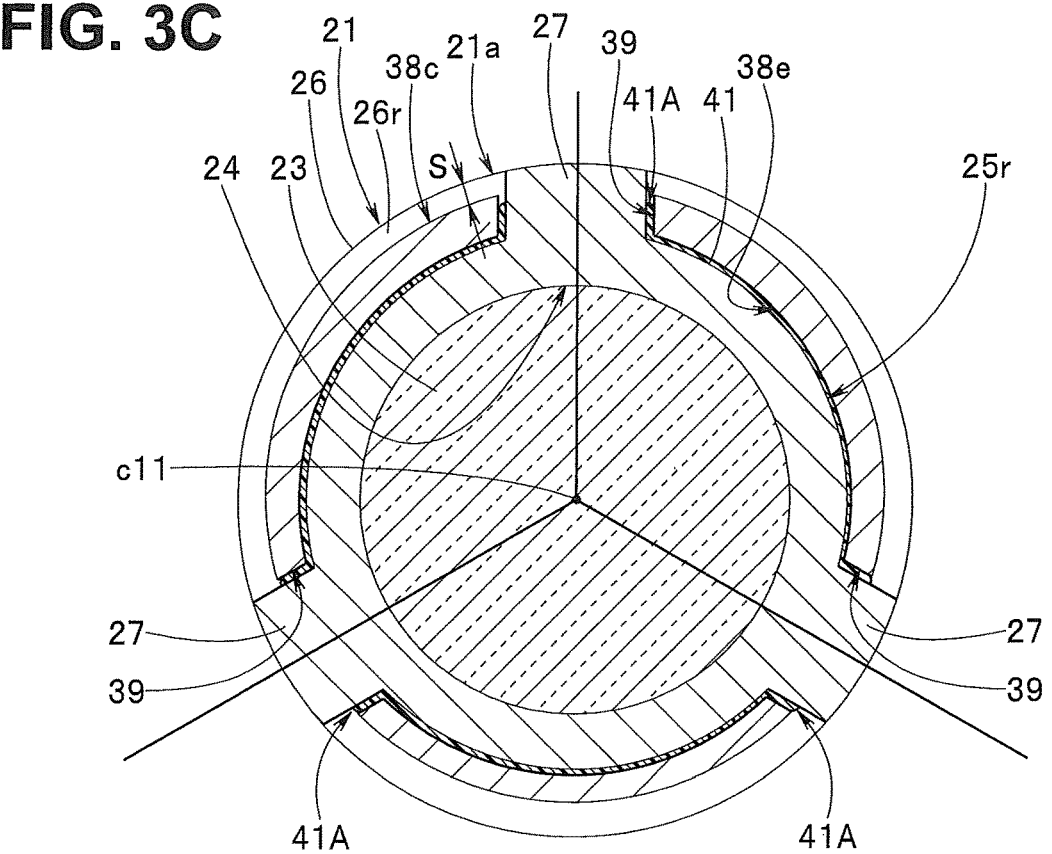
FIG. 3C is a cross-sectional view along a Y3C-Y3C line in FIG. 3B.

The holding portion 27 is an engaging portion which is projected outward from the proximal-end-side outer circumferential face 25r by a predetermined amount and extends in the circumferential direction. The holding portion 27 is formed projecting from the proximal end face 26r side of the projecting portion 26 having a second thickness t2 set thicker than the first thickness t1 to the proximal end side along the longitudinal axis beforehand. As shown in FIG. 3C, three holding portions 27 are provided at equal intervals in the circumferential direction, for example, at intervals of 120 degrees.

Outer circumferential faces of the holding portions 27 constitute the second area outer circumferential face 21a which can be the objective lens unit jig grasping face, similarly to the outer circumferential face of the projecting portion 26. In other words, in the present embodiment, the outer circumferential faces of the holding portions 27 and the outer circumferential face of the projecting portion 26 constitute the second area outer circumferential face 21a and can constitute the objective lens unit jig grasping face.

In the case of grasping the second area outer circumferential face 21a by an objective lens unit jig 40A, it is possible to reduce deformation of the optical frame 21 because the thickness is thicker than the first area.

Note that width and length dimensions of the holding portions 27 are set so that such an area that, in consideration of an area of the outer circumferential face of the projecting portion 26, makes it possible to certainly and stably grasp the second area outer circumferential face 21a by the objective lens unit jig (hereinafter briefly referred to as the first jig) 40A is obtained.

As shown in FIG. 3B, the image pickup unit 30 is provided with the image pickup device frame 31 which is a second holding frame, an image pickup device 32, a circuit board 33 on which electronic parts not shown are implemented, a signal cable (not shown) and the like. The image pickup device 32 is a CCD, a CMOS or the like.

A second through hole 34 is formed in the image pickup device frame 31 along the longitudinal axis. In the second through hole 34, the image pickup device 32 constituting the second optical system, cover lenses 35a and 35b fixed to a front face of a light receiving face (not shown) of the image pickup device 32 by transparent adhesive and the like are coaxially arranged.

Reference symbol c11 indicates an optical axis of the optical unit 11. An optical axis (reference symbol a21 in FIG. 3D) of the optical system provided in the optical frame 21 and an optical axis (reference symbol a31 in FIG. 3D) of the optical system provided in the image pickup device frame 31 are coaxial. Reference symbol 36 indicates sealing resin, and the sealing resin is filled in an exterior frame 37.

Figure 3D:
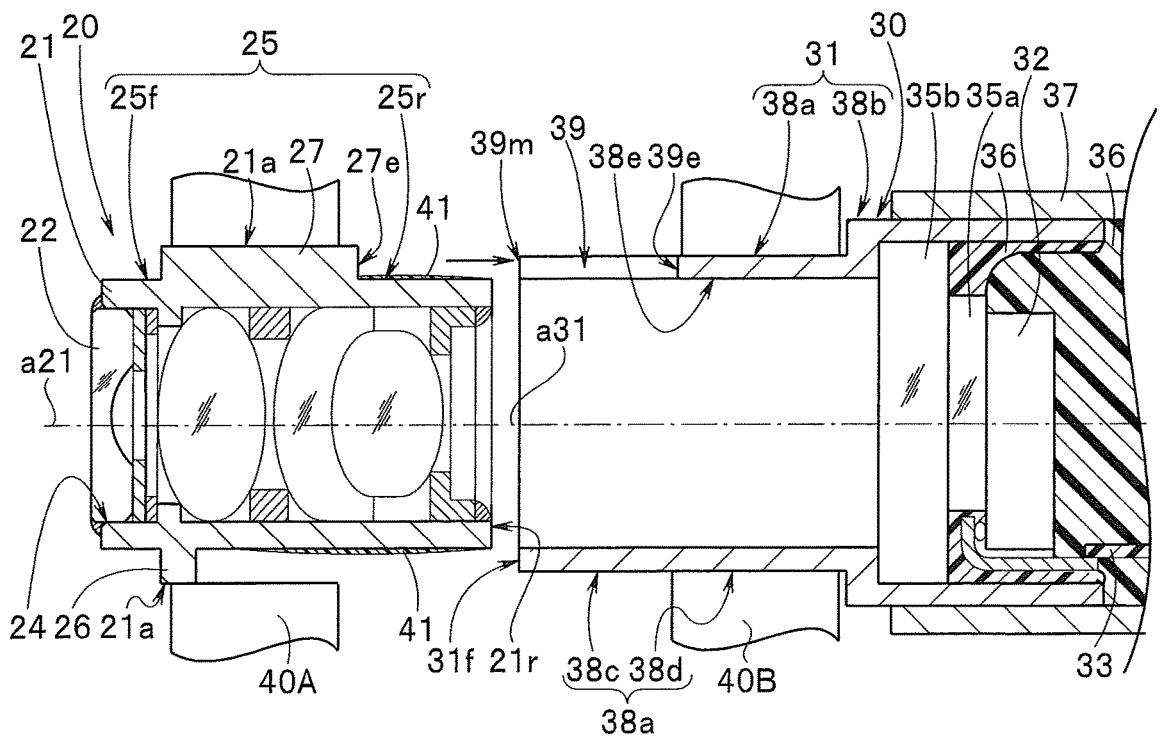
FIG. 3D is a diagram illustrating assembly between the optical frame of the objective lens unit and the image pickup device frame of the image pickup unit.

As shown in FIGS. 3A, 3B and 3D, the image pickup device frame 31 is provided with a distal-end-side frame body 38a constituting the distal end side and a proximal-end-side frame body 38b constituting the proximal end side.

As shown in FIG. 3C, the distal-end-side frame body 38a is provided with three notches 39 arranged apart as accommodating portions configured to accommodate the holding portions 27.

As shown in FIG. 3A, the notches 39 have opening portions 39m as openings, respectively, on an image pickup device frame distal end face 31f facing the projecting portion proximal end face 26r of the optical frame 21.

The holding portions 27 pass through the opening portions 39m and are accommodated and arranged in the notches 39 as shown by an arrow in FIG. 3D. Each of the notches 39 is formed along the longitudinal axis similarly to the holding portions 27. As shown in FIG. 3A, a width of the notches 39 including a width of the opening portions 39m is set larger than the width of the holding portions 27 beforehand.

Therefore, in an assembled state in which the holding portions 27 are accommodated in the notches 39, clearances where adhesive pools (see reference symbol 41A in FIGS. 3B and 3C) are provided are obtained between inner walls of the notches 39 and side faces of the holding portions 27.

Note that a relationship between the length of the holding portions 27 in the longitudinal axis direction and a cut depth of the notches 39 in the longitudinal axis direction is set to one of the following two. In one setting, the image pickup device frame distal end face 31f comes into contact with the projecting portion proximal end face 26r of the optical frame 21 before notch end faces 39e of the notches 39 come into contact with proximal end faces 27e of the holding portions 27 arranged in the notches 39, respectively. In the other setting, the proximal end faces 27e come into contact with the notch end faces 39e, respectively, before the image pickup device frame distal end face 31f comes into contact with the projecting portion proximal end face 26r.

As shown in FIGS. 3A and 3D, the distal-end-side frame body 38a has a frame body distal-end-side outer circumferential face 38c and a frame body proximal-end-side outer circumferential face 38d, and the frame body proximal-end-side outer circumferential face 38d can be an image pickup unit jig grasping face. As shown in FIGS. 3A and 3D, the frame body proximal-end-side outer circumferential face 38d constitutes the proximal end side of the notch end faces 39e of the notches 39 formed on the distal-end-side frame body 38a. A length of the frame body proximal-end-side outer circumferential face 38d in the longitudinal axis direction is set longer than a length of a second jig 40B in the longitudinal axis direction.

Note that, as shapes of the jigs 40A and 40B, such ring shapes that inner circumferential faces are grasping faces are preferable when the three holding portions 27 are provided at equal intervals. The shapes of the jigs 40A and 40B are not limited to ring shapes, and the jigs 40A and 40B may be plate members. The shapes of the plate members are flat, V-shaped or the like.

An inner circumferential face 38e of the distal-end-side frame body 38a shown in FIGS. 3B and 3C is a second mating face. By the proximal-end-side outer circumferential face 25r, which is the first mating face of the optical frame 21 described above, internally being mated with the inner circumferential face 38e, a mated portion is configured. In the present embodiment, in the state in which the proximal-end-side outer circumferential face 25r of the optical frame 21 is mated inside the inner circumferential face 38e of the distal-end-side frame body 38a, the holding portions 27 are arranged in the notches 39, and the second area outer circumferential face 21a projects from the frame body distal-end-side outer circumferential face 38c by a predetermined dimension S as shown in FIG. 3C. In other words, an outer diameter of the second area outer circumferential face 21a is set larger than an outer diameter of the frame body distal-end-side outer circumferential face 38c.

Note that, in the present embodiment, the frame body distal-end-side outer circumferential face 38c and the frame body proximal-end-side outer circumferential face 38d are coplanar. However, a thickness of the frame body proximal-end-side outer circumferential face 38d may be set thicker than a thickness of the frame body distal-end-side outer circumferential face 38c.

According to the above configuration, it is prevented that, at the time of causing the first jig 40A to be arranged coming into contact with the second area outer circumferential face 21a, the first jig 40A comes into contact with the frame body distal-end-side outer circumferential face 38c other than the second area outer circumferential face 21a. In other words, the first jig 40A can certainly grasp at least the outer circumferential face 38af of the projecting portion 26 of the second area outer circumferential face 21a without coming into contact with the frame body distal-end-side outer circumferential face 38c Note that the number of the holding portions 27 and the notches 39 is not limited to three in the circumferential direction but is only required to be two or more, that is, plural.

Here, assembly between the optical frame 21 and the image pickup device frame 31 will be described with reference to FIG. 3D.

At the time of assembling the optical frame 21 and the image pickup device frame 31, a worker grasps the second area outer circumferential face 21a of the optical frame 21 by the first jig 40A first as shown in FIG. 3D. The worker grasps the frame body proximal-end-side outer circumferential face 38d of the image pickup device frame 31 by the second jig 40B.

As a result, the optical frame 21 is grasped by the first jig 40A in a stable state. The image pickup device frame 31 is grasped by the second jig 40B in a stable state. In this grasped state, the optical frame 21 and the image pickup device frame 31 are arranged facing each other in a state in which the optical axis a21 of the optical frame 21 and the device axis a31 of the image pickup device frame 31 correspond to each other. Then, the optical frame 21 is in a state of moving along the optical axis a21, and the image pickup device frame 31 is in a state of moving along the device axis a31.

The worker applies adhesive 41 to the proximal-end-side outer circumferential face 25r of the optical frame 21 beforehand at the time of assembling the optical frame 21 and the image pickup device frame 31. Then, the worker gradually brings the jigs 40A and 40B close to each other. Then, an optical frame proximal end face 21r of the optical frame 21 is smoothly fitted inside the inner circumferential face 38e of the distal-end-side frame body 38a. Then, a part of the adhesive 41 applied to the proximal-end-side outer circumferential face 25r is applied between mating parts, and remaining adhesive 41 is pushed back to the distal end side by the image pickup device frame distal end face 31f.

Then, by the worker further bringing the jigs 40A and 40B close to each other, the optical frame proximal end face 21r is moved to the depth inside the inner circumferential face 38e. At this time, a part of the adhesive 41 is applied between the mating parts, and remaining adhesive 41 is further pushed back to the distal end side by the image pickup device frame distal end face 31f. The proximal end face 27e sides of the holding portions 27 enter the notches 39 from the opening portions 39m, and the holding portions 27 are accommodated into the notches 39. At this time, a part of the adhesive 41 is applied between the mating parts, and remaining adhesive 41 is pushed back into the clearances between the inner walls of the notches 39 and the side faces of the holding portions 27 by the notch end faces 39e.

The worker performs focus adjustment in the direction of the optical axis c11 by changing the mating length while confirming a positional relationship between the holding portions 27 and the notches 39. After completion of the focus adjustment, the holding portions 27 are accommodated in the notches 39 as shown in FIGS. 3A and 3B. At this time, as shown in FIG. 3B, a mated state in which the mating length between the proximal-end-side outer circumferential face 25r of the optical frame 21 and the inner circumferential face 38e of the distal-end-side frame body 38a is sufficiently secured, and bond strength is sufficient is obtained.

In this mated state, a part of the adhesive 41 is applied between the mating parts. The adhesive 41 pushed back by the image pickup device frame distal end face 31f becomes adhesive pools 41A in a space between the device frame distal end face 31f and the projecting portion proximal end face 26r. The adhesive 41 pushed back by the notch end faces 39e becomes adhesive pools 41A in the clearances between the notch end faces 39e and the proximal end faces 27e.

Then, by the adhesive 41 applied between the mating parts, the adhesive pools 41A in the space and the adhesive pools 41A in the clearances being cured, the optical frame 21 and the image pickup device frame 31 are firmly and integrally fixed.

Thus, the optical frame 21 is provided with the plurality of holding portions 27, and the image pickup device frame 31 is provided with the notches 39 configured to accommodate the holding portions 27. The second area outer circumferential face 21a is made the objective lens unit jig grasping face, and the frame body proximal-end-side outer circumferential face 38d on the proximal end side of the notches 39 is made the image pickup unit jig grasping face. In addition, an outer diameter of the objective lens unit jig grasping face is set larger than an outer diameter of the image pickup unit jig grasping face.

Thereby, it is possible to, without increasing a length of the optical frame 21 and a length of the image pickup device frame 31, obtain the second area outer circumferential face 21a configured to have such an area that the objective lens unit jig grasping face, which is a range grasped by the first jig 40A, can be stably grasped by the outer circumferential face of the projecting portion 26 and, additionally, the outer circumferential faces of the holding portions 27.

As a result, a state of easily and certainly grasping the second area outer circumferential face 21a of the optical frame 21 by the first jig 40A can be obtained.

Further, the outer diameter of the second area outer circumferential face 21a is set larger than the outer diameter of the frame body distal-end-side outer circumferential face 38c. As a result, a problem of the first jig 40A coming into contact with the image pickup device frame 31 when grasping the second area outer circumferential face 21a is solved, and a stable grasping state can be obtained.

Furthermore, as described above, it is possible to certainly grasp the optical frame 21 by the first jig 40A in a stable state, and, in addition, it is possible to certainly grasp the image pickup device frame 31 by the second jig 40B in a stable state. As a result, it is possible to certainly prevent occurrence of misalignment between the frames and stably perform mating length adjustment at the time of performing assembly to realize secure focus adjustment.

The mated portion between the optical frame 21 and the image pickup device frame 31 described above is configured by the proximal-end-side outer circumferential face 25r of the optical frame 21 being mated inside the inner circumferential face 38e of the distal-end-side frame body 38a and is in a state in which the mating length L is sufficiently secured as shown in FIG. 3B. Then, by the adhesive 41 applied between the mating parts, the adhesive pools 41A in the space and the adhesive pools 41A in the clearances being cured, the optical frame 21 and the image pickup device frame 31 are firmly and integrally fixed.

In the configuration described above, it is possible to grasp the optical frame 21 by the first jig 40A in a stable state; it is possible to grasp the image pickup device frame 31 by the second jig 40B in a stable state; and the mating length L is secured to obtain a sufficient mated state. In the case where it is possible to stably grasp the optical frame 21 and the image pickup device frame 31 by the jigs 40A and 40B as described above, the mating length may be set to a minimum required length shorter than L to obtain a sufficient mated state.

Figure 3E:
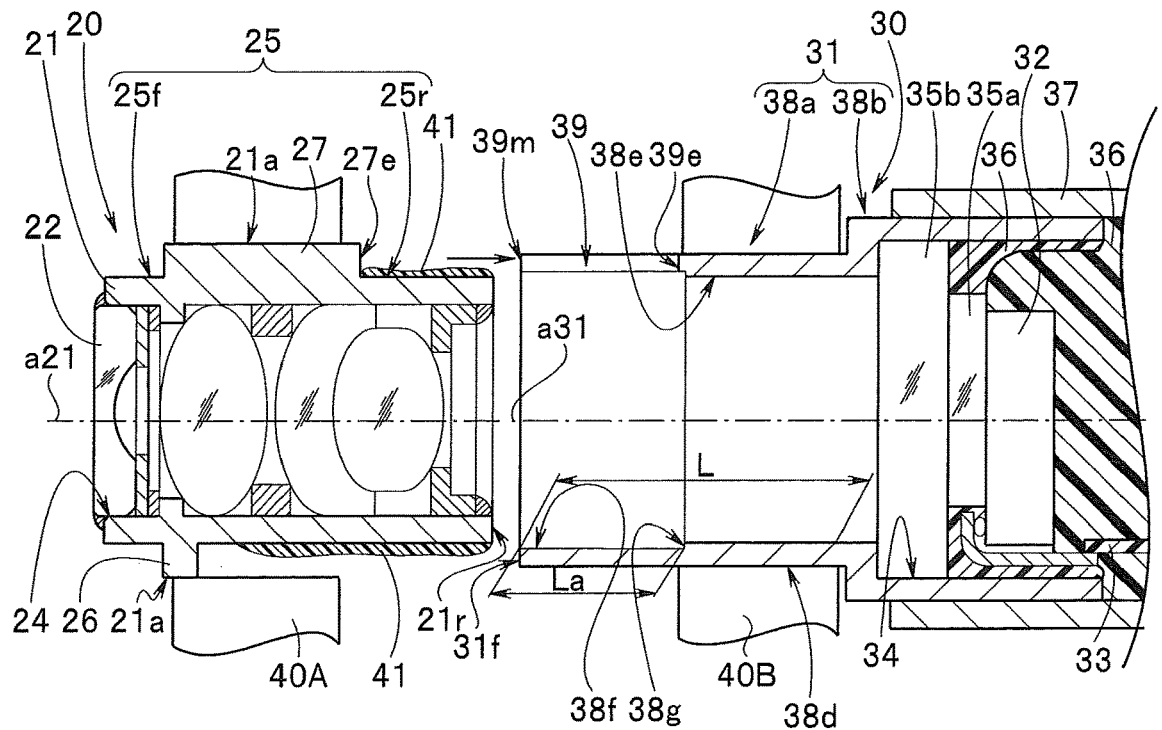
FIG. 3E is a diagram illustrating assembly between the optical frame and the image pickup device frame of the image pickup unit, where a gap is provided between mating parts.

In this case, a recess portion 38f is provided on the inner circumferential face 38e of the image pickup device frame 31 as a gap forming portion as shown in FIG. 3E. The recess portion 38f has an inner circumferential face with an inner diameter set slightly larger than an inner diameter of the inner circumferential face 38e. For the recess portion 38f, a distance from the image pickup device frame distal end face 31f to a recess portion bottom face 38g is set to La. According to this configuration, the mating length is adjusted from L to (L-La). The adjusted (L-La) is a mating length with which a stable bond strength can be obtained in an assembled state.

Note that the recess portion 38f forms a dual-purpose gap (hereinafter briefly referred to as a gap) S1 (see FIG. 3F) described later, which serves as both of a relief portion and an adhesive filling gap, between the inner circumferential face of the recess portion 38f and the proximal-end-side outer circumferential face 25r.

The image pickup device frame 31 provided with the recess portion 38f on the inner circumferential face 38e is grasped by the second jig 40B, and the optical frame 21 is grasped by the first jig 40A. Thereby, the optical axis a21 and the device axis a31 correspond to each other, and the optical frame 21 and the image pickup device frame 31 are in the state of being arranged facing each other, as described above. At this time, the optical frame 21 is in the state of moving along the optical axis a21, and the image pickup device frame 31 is in the state of moving along the device axis a31 as described above.

The worker applies the adhesive 41 to the proximal-end-side outer circumferential face 25r of the optical frame 21 beforehand at the time of assembling the optical frame 21 and the image pickup device frame 31. When the worker gradually brings the jigs 40A and 40B close to each other, the optical frame proximal end face 21r of the optical frame 21 is arranged, being loosely fitted in the recess portion 38f of the distal-end-side frame body 38a. Then, by the worker further bringing the jigs 40A and 40B close to each other, the optical frame proximal end face 21r moves toward the recess portion bottom face 38g in the recess portion 38f in the loosely mated state. The proximal end face 27e sides of the holding portions 27 enter the notches 39 from the opening portions 39m, and the holding portions 27 are accommodated into the notches 39.

After that, after the optical frame proximal end face 21r reaches the recess portion bottom face 38g, the proximal-end-side outer circumferential face 25r is fitted inside the inner circumferential face 38e. Then, a part of the adhesive 41 applied to the proximal-end-side outer circumferential face 25r is applied between the mating parts, and remaining adhesive 41 is scraped by a step portion between the recess portion bottom face 38g and the inner circumferential face 38e, and the adhesive 41 is pushed back into the gap S1 and the clearances between the side faces of the holding portions 27 and the inner walls of the notches 39.

Figure 3F:
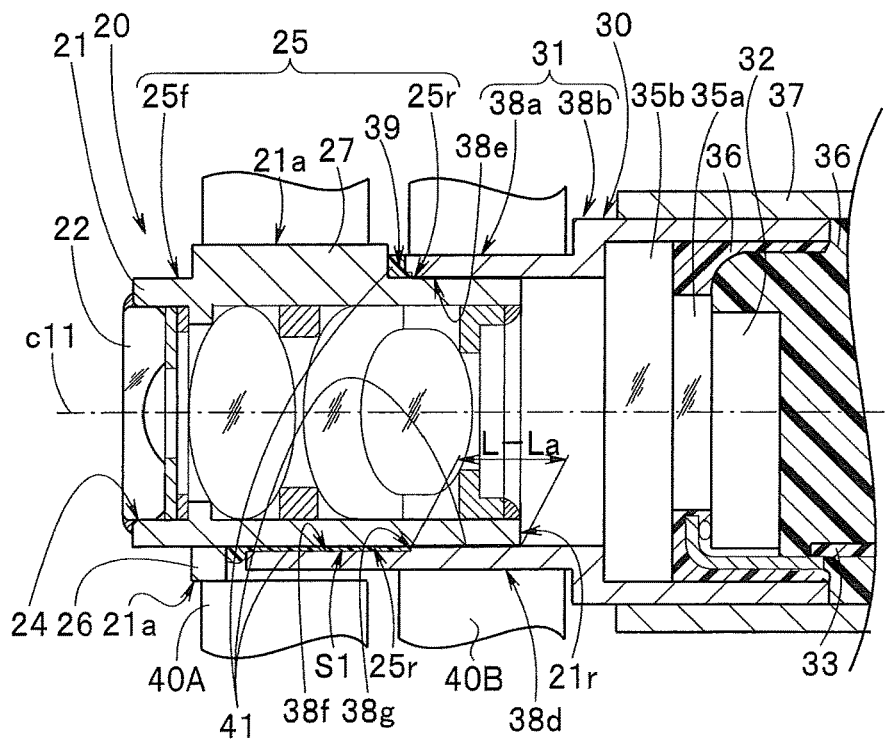
FIG. 3F is a diagram showing a state in which the optical frame and the image pickup device frame with the gap provided between the mating parts are integrally fixed.

The worker performs focus adjustment in the direction of the optical axis c11 by changing the mating length while confirming the positional relationship between the holding portions 27 and the notches 39. After completion of the focus adjustment, the holding portions 27 are accommodated in the notches 39 as shown in FIGS. 3A and 3B. At this time, as shown in FIG. 3F, the proximal-end-side outer circumferential face 25r of the optical frame 21 and the inner circumferential face 38e of the distal-end-side frame body 38a are in a mated state with the mating length (L-La) with which a necessary bond strength can be obtained.

In this mated state, a part of the adhesive 41 is applied between the mating parts. The adhesive 41 scraped by the step portion is filled into the gap S1 and becomes adhesive pools 41A in the clearances.

Then, by the adhesive 41 applied between the mating parts, the adhesive 41 in the gap S1 and the adhesive pools 41A in the clearances being cured, the optical frame 21 and the image pickup device frame 31 are firmly and integrally fixed.

Thus, in addition to providing the optical frame 21 with the plurality of holding portions 27, providing the image pickup device frame 31 with the notches 39 configured to accommodate the holding portions 27, and causing the second area outer circumferential face 21a to be the objective lens unit jig grasping face, the recess portion 38f forming the gap S1 is provided inside the inner circumferential face 38e of the distal-end-side frame body 38a constituting the mated portion.

Thereby, at the time of performing assembly by gradually bringing the first jig 40A certainly grasping the optical frame 21 and the second jig 40B certainly grasping the image pickup device frame 31 close to each other, a distance of movement in a state of being fitted can be decreased by an amount corresponding to the gap S1, that is, by the distance La to further improve workability.

Further, by the adhesive 41 applied to the proximal-end-side outer circumferential face 25r is filled in the gap S1, bonding fixation between the optical frame 21 and the image pickup device frame 31 is performed by the adhesive 41 applied between the mating parts of the proximal-end-side outer circumferential face 25r and the inner circumferential face 38e, which constitute a mated portion with (L-La), and the adhesive 41 filled in the gap S1. Thereby, resistance to external forces can be significantly improved.

Note that the intervals among the holding portions 27 and among the notches 39 are not limited to equal intervals. In other words, the plurality of holding portions 27 and the notches 39 are required only to be provided so that the holding portions 27 are accommodated into corresponding notches 39 through corresponding opening portions 39m, respectively, at the time of causing the optical frame 21 and the image pickup device frame 31 to mate with each other.

Another configuration example of an optical unit will be described with reference to FIGS. 4A to 4D.

In the embodiment shown in FIGS. 3A to 3F described above, the optical frame 21, which is one holding frame, is provided with the holding portions 27 as engaging portions, and the image pickup device frame 31, which is the other holding frame, is provided with the notches 39 as accommodating portions configured to accommodate the holding portions 27. A configuration is made in which the outer circumferential faces of the holding portions 27 and the outer circumferential face of the projecting portion 26 can constitute the objective lens unit jig grasping face configured to decrease deformation of the optical frame 21.

Figure 4A:
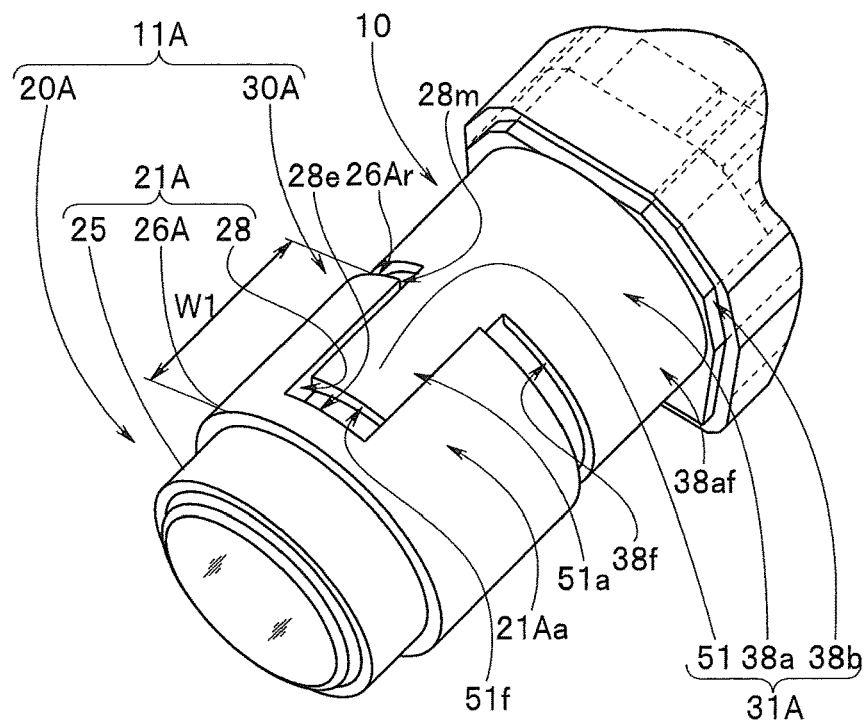
FIG. 4A is a diagram illustrating another configuration example of an optical unit of an image pickup apparatus.

In comparison, in the present embodiment, an image pickup device frame 31A, which is one holding frame of an optical unit 11A, is provided with a nail member (hereinafter referred to as a nail portion) 51 which functions as an image pickup device frame mating face for securing bond strength, as an engaging portion as shown in FIG. 4A. An optical frame 21A, which is the other holding frame, is provided with an accommodating recess portion 28 configured to accommodate the nail portion 51. Reference symbol 51a indicates a nail member surface.

In the present embodiment, a nail portion mating face (see reference symbol 51b in FIGS. 4B and 4D), which is a mating face of the nail portion 51, is a part of a second mating face. Therefore, the nail portion mating face 51b is in a state of mating with a bottom face (see reference symbol 28d in FIGS. 4C and 4D) of the accommodating recess portion 28 of the optical frame 21, which is a first mating face, and constitutes a part of a mated portion.

Figure 4B:
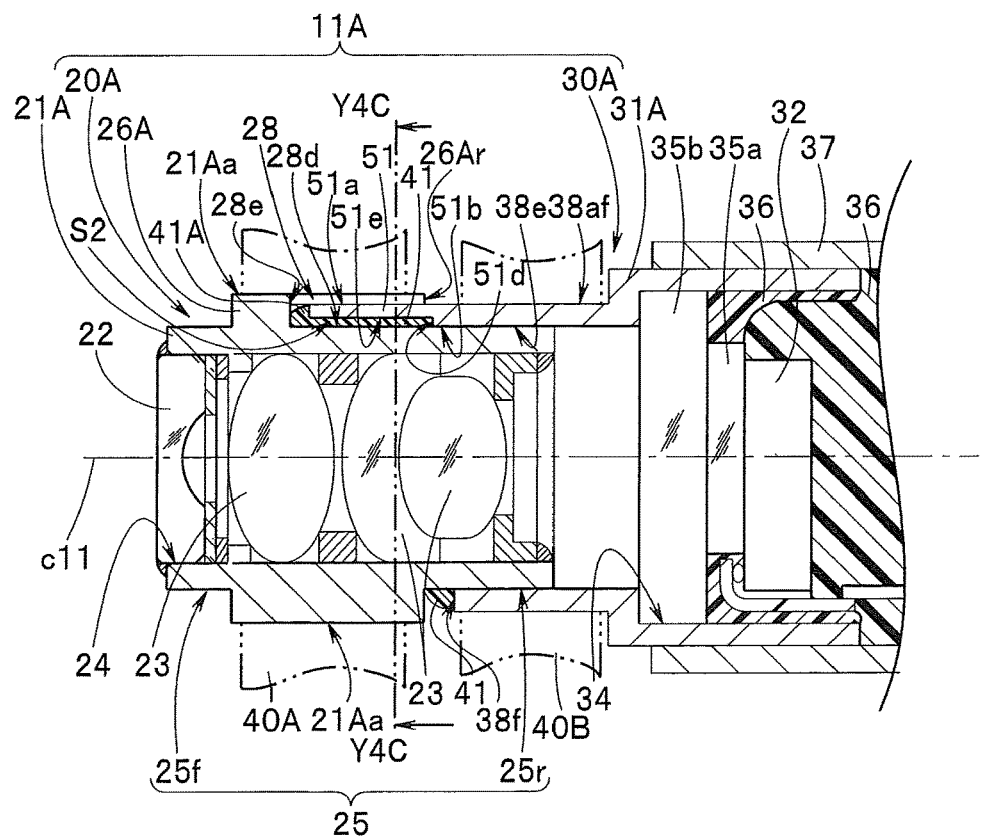
FIG. 4B is a longitudinal sectional view illustrating the optical unit of FIG. 4A and is a diagram illustrating a configuration in which, without increasing lengths of frame members, an image pickup device frame mating face is provided in addition to an inner circumferential face of a frame body.

As shown in FIGS. 4A and 4B, an optical unit 11A of the present embodiment is provided with an objective lens unit 20A and an image pickup unit 30A.

The distal-end-side frame body 38a of an image pickup device frame 31A of the image pickup unit 30A is provided with the nail portion 51. The nail portion 51 is an engaging portion projecting from a frame body distal end face 38f of the distal-end-side frame body 38a by a length LB (see FIG. 4D) along the longitudinal axis.

In the present embodiment, the image pickup device frame 31A is configured with the nail portion 51, the distal-end-side frame body 38a and the proximal-end-side frame body 38b. An outer circumferential face 38af of the distal-end-side frame body 38a corresponds to the frame body proximal-end-side outer circumferential face 38d described above and can be an image pickup unit jig grasping face.

Figure 4C:
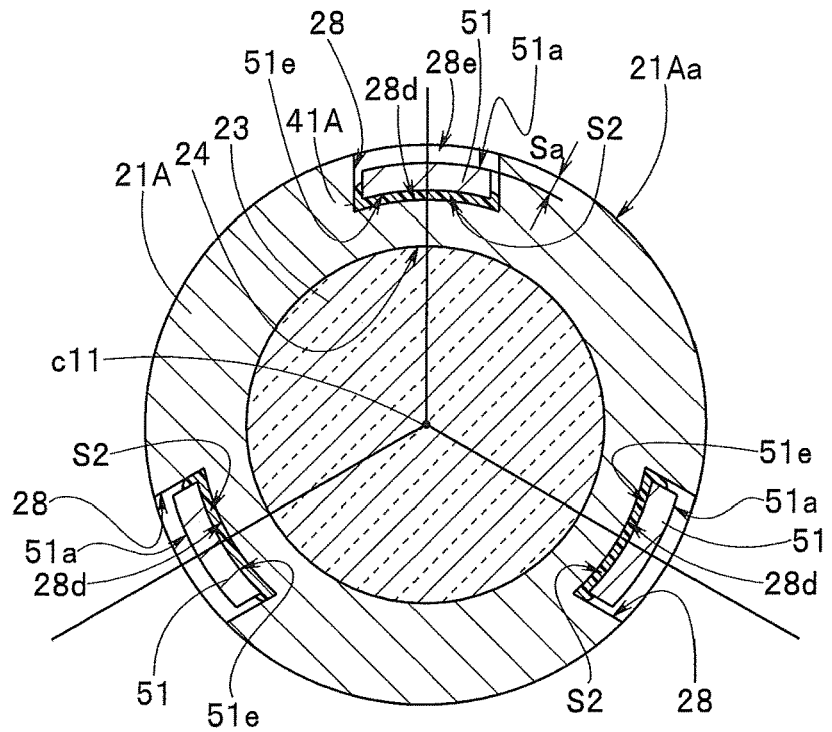
FIG. 4C is a cross-sectional view along a Y4C-Y4C line in FIG. 4B.
Figure 4D:
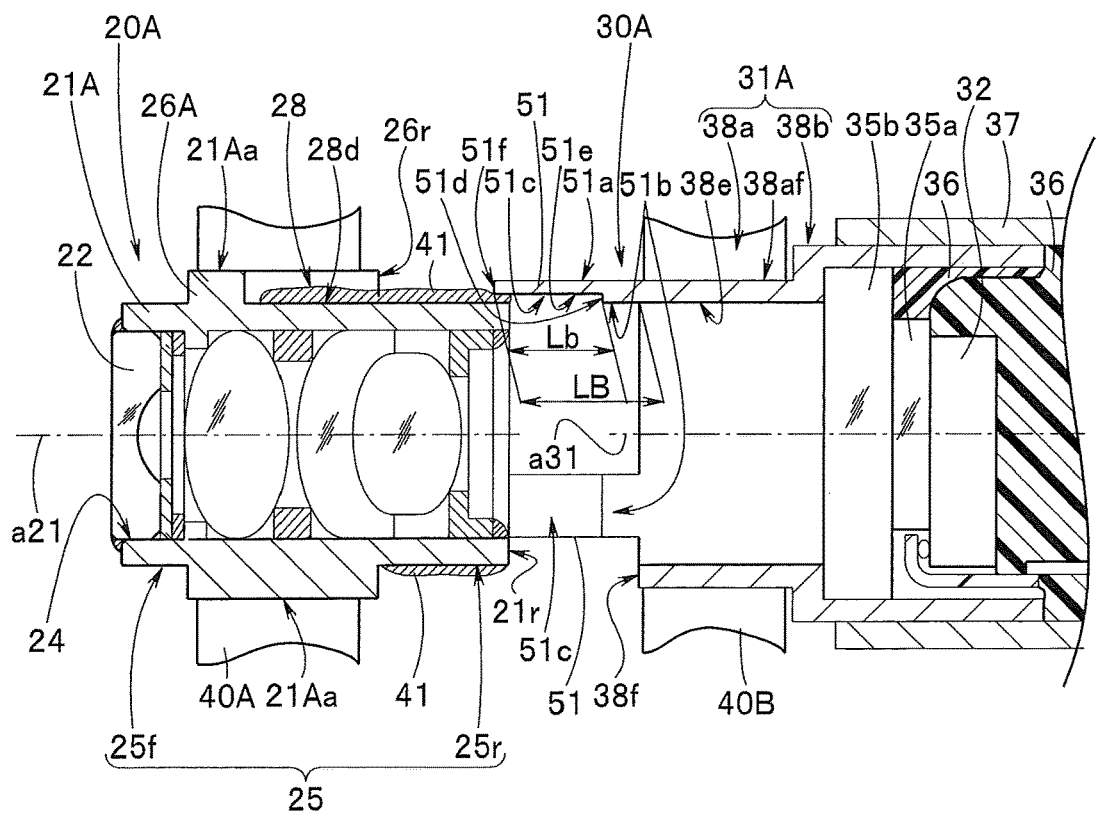
FIG. 4D is a diagram illustrating assembly between an optical frame of an objective lens unit and an image pickup device frame of an image pickup unit.

As shown in FIGS. 4B and 4D, the nail portion 51 has a nail portion mating face 51b configured to function as the image pickup device frame mating face and a nail recess portion 51c as a gap forming portion on an inner circumferential face which is a back side of a nail portion outer circumferential face. The nail portion mating face 51b is coplanar with the inner circumferential face 38e. In comparison, the nail recess portion 51c has an inner circumferential face with an inner diameter set slightly larger than an inner diameter of the inner circumferential face 38e.

For the nail recess portion 51c, a distance from a distal end face 51f of the nail portion 51 to a recess portion other face 51d is set to Lb as shown in FIG. 4D. As a result, the nail portion mating face 51b of the nail portion 51 is within a range of (LB-Lb). Note that, as shown in FIGS. 4B and 4C, the nail recess portion 51c forms a gap S2 having a function that is substantially similar to the function of the above-described gap S1 that serves as both of a relief portion and an adhesive filling gap, between a recess portion inner face 51e and the bottom face 28d of the accommodating recess portion 28.

As shown in FIG. 4D, an area of the nail portion mating face 51b is represented by a width dimension and length (LB-Lb) of the nail portion 51. Therefore, the area of the nail portion mating face 51b is appropriately set so that a mated state in which stable bond strength can be secured in an assembled state can be obtained. In the present embodiment, three nail portions 51 are provided, for example, at equal intervals in the circumferential direction similarly to the embodiment described above (see FIG. 4C).

Note that, as described above, the number of nail portions 51 is not limited to three at equal intervals.

In comparison, the optical frame 21A of the objective lens unit 20A is provided with the frame body 25 described above, a wide-width projecting portion 26A which is a second area and the accommodating recess portions 28. A width W1 of the wide-width projecting portion 26A is wider than a width W of the projecting portion 26 described above, and an outer surface of the wide-width projecting portion 26A is a second area outer circumferential face 21Aa and can be an objective lens unit jig grasping face.

The accommodating recess portions 28 have opening portions 28m on a projecting portion proximal end face 26Ar facing the frame body distal end face 38f of the image pickup device frame 31A. The nail portions 51 pass through the opening portions 28m, and are accommodated and arranged in the accommodating recess portions 28. Therefore, each of the accommodating recess portions 28 is formed along the longitudinal axis. A width of the opening portions 28m is set larger than the width of the nail portions 51 beforehand. Therefore, in an assembled state in which the nail portions 51 are accommodated in the accommodating recess portions 28, clearances where adhesive pools (see reference symbol 41A in FIGS. 4B and 4C) are provided are obtained between inner walls of the accommodating recess portions 28 and side faces of the nail portions 51.

Note that a relationship between the length of the nail portions 51 in the longitudinal axis direction and a cut depth of the accommodating recess portions 28 in the longitudinal axis direction is set to one of the following two. In one setting, the frame body distal end face 38f comes into contact with a projecting portion proximal end face 26Ar of the optical frame 21A, respectively, before terminal end faces 28e of the accommodating recess portions 28 come into contact with distal end faces 51f of the nail portions 51 arranged in the accommodating recess portions 28, respectively. In the other setting, the distal end faces 51f of the nail portions 51 come into contact with the terminal end faces 28e, respectively, before the frame body distal end face 38f comes into contact with the projecting portion proximal end face 26Ar.

In the present embodiment, in a state in which the proximal-end-side outer circumferential face 25r of the optical frame 21A is arranged mating with the inner circumferential face 38e of the distal-end-side frame body 38a, and the nail portions 51 are arranged in the accommodating recess portions 28, the second area outer circumferential face 21Aa of the wide-width projecting portion 26A projects from nail portion surfaces 51a of the nail portions 51 arranged in the accommodating recess portions 28 by a predetermined dimension Sa. In other words, an outer diameter of the second area outer circumferential face 21Aa is set larger than an outer diameter of the nail portion surfaces 51a of the nail portions 51.

According to the above configuration, it is prevented that, at the time of causing the first jig 40A to be arranged coming into contact with the second area outer circumferential face 21Aa, the first jig 40A comes into contact with the nail portions 51. Note that the nail portion surfaces 51a are a part of the outer circumferential face 38af of the distal-end-side frame body 38a, in other words, the nail portion surfaces 51a and the outer circumferential face of the distal-end-side frame body 38a are coplanar.

Here, assembly between the optical frame 21A and the image pickup device frame 31A will be described with reference to FIG. 4D.

At the time of assembling the optical frame 21A and the image pickup device frame 31A, the worker grasps the second area outer circumferential face 21Aa of the wide-width projecting portion 26A of the optical frame 21A with the first jig 40A and grasps the outer circumferential face 38af of the distal-end-side frame body 38a of the image pickup device frame 31A with the second jig 40B first as shown in FIG. 4D.

As a result, the optical frame 21A is grasped by the first jig 40A in a stable state, and the image pickup device frame 31A is grasped by the second jig 40B in a stable state. In this grasped state, the optical frame 21A and the image pickup device frame 31A are arranged facing each other in a state in which the optical axis a21 of the optical frame 21A and the device axis a31 of the image pickup device frame 31A correspond to each other. Then, the optical frame 21A is in a state of moving along the optical axis a21, and the image pickup device frame 31A is in a state of moving along the device axis a31.

The worker applies adhesive 41 to the proximal-end-side outer circumferential face 25r and the bottom faces 28d of the accommodating recess portions 28 beforehand at the time of assembling the optical frame 21A and the image pickup device frame 31A. Then, the worker gradually brings the jigs 40A and 40B close to each other. Then, the optical frame proximal end face 21r of the optical frame 21A are arranged, being loosely fitted in the nail recess portions 51c of the nail portions 51, and, after that, the optical frame proximal end face 21r is smoothly fitted inside the inner circumferential face 38e of the distal-end-side frame body 38a and moved toward the depth. Further, the distal end faces 51f of the nail portions 51 pass through the opening portions 28m as openings of the accommodating recess portions 28 and move in the accommodating recess portions 28.

At this time, a part of the adhesive 41 applied to the proximal-end-side outer circumferential face 25r is applied between the mating parts, and remaining adhesive 41 is pushed back in a distal end direction of the optical frame 21A by the frame body distal end face 38f. A part of the adhesive 41 applied to the bottom faces 28d of the accommodating recess portions 28 is applied between the mating parts, and remaining adhesive 41 is scraped by step portions between the recess portion inner faces 51e and the nail portion mating faces 51b and filled into the gaps S2 and the clearances.

Then, by the jigs 40A and 40B being further brought close to each other by the worker, the proximal-end-side outer circumferential face 25r is mated inside the inner circumferential face 38e. At this time, a part of the adhesive 41 applied to the proximal-end-side outer circumferential face 25r is applied between the mating parts; another part of the adhesive 41 becomes adhesive pools 41A in the clearances; and remaining adhesive 41 is filled into the gaps S2.

The worker performs focus adjustment in the direction of the optical axis c11 by changing the mating length while confirming a positional relationship between the nail portions 51 and the accommodating recess portions 28. After completion of the focus adjustment, the nail portions 51 are accommodated in the accommodating recess portions 28 as shown in FIGS. 4A and 4B. At this time, as shown in FIG. 4B, the nail portion mating faces 51b of the nail portions 51 are arranged on the bottom faces 28d of the accommodating recess portions 28, and a mated state with a sufficient bond strength is obtained.

Thereby, the proximal-end-side outer circumferential face 25r and the inner circumferential face 38e of the distal-end-side frame body 38a constitute a mated portion; the nail portion mating faces 51b of the nail portions 51 and the bottom faces 28d of the accommodating recess portions 28 constitute mated portions; and, the optical frame 21A and the image pickup device frame 31A are in an assembled state having a sufficient mated state.

Thus, the image pickup device frame 31A is provided with the nail portions 51, and the optical frame 21A is provided with the accommodating recess portions 28 configured to accommodate the nail portions 51. The nail portion mating faces 51b of the nail portions 51 and the bottom faces 28d of the accommodating recess portions 28 are made a part of mated portions. Thereby, without increasing lengths of the optical frame 21A and the image pickup device frame 31A, the nail portion mating faces 51b of the nail portions 51 and the bottom faces 28d of the accommodating recess portions 28 are caused to constitute mated portions in addition to a mated portion formed by the proximal-end-side outer circumferential face 25r and the inner circumferential face 38e of the distal-end-side frame body 38a, so that a sufficient mated state can be obtained.

Further, by providing the nail recess portions 51c on a distal end side with respect to the nail portion mating faces 51b of the nail portions 51, the adhesive 41 applied to the bottom faces 28d of the accommodating recess portions 28 beforehand can be filled into the gaps S2 and gaps around the nail recess portions 51c. By the adhesive 41 in the gaps S2, the adhesive 41 in the adhesive pools 41A and the adhesive 41 between the mating parts being cured, the optical frame 21A and the image pickup device frame 31A is firmly and integrally fixed, so that the resistance to external forces can be significantly improved.

Note that, by the second area outer circumferential face 21Aa of the wide-width projecting portion 26A projecting from the nail portion surfaces 51a of the nail portions 51 arranged in the accommodating recess portions 28 by the dimension Sa, it is prevented that the first jig 40A comes into contact with the nail portions 51 of the image pickup device frame 31 in a state in which a projecting portion outer circumferential face 26Aa of the wide-width projecting portion 26A is grasped by the first jig 40A.

Therefore, it is possible to certainly grasp the optical frame 21A with the first jig 40A and certainly grasp the image pickup device frame 31A with the second jig 40B to perform secure focus adjustment.

In the embodiments described above, the number of holding frames is two. However, for example, in the case of a stereoscopic endoscope, two optical frames and one image pickup device frame are provided, and positioning/fixation of the two optical frames and focus adjustment between the optical frames and the image pickup device frame are performed.

A different configuration example of an optical unit will be described with reference to FIGS. 5A to 5C.

In the embodiment shown in FIGS. 3A to 3C and the embodiment shown in FIGS. 4A to 4C described above, two unit jigs are used to grasp two holding frames, respectively, to perform assembly. However, there may be a case where three unit jigs are used to grasp three holding frames, respectively, to perform assembly.

Figure 5A:
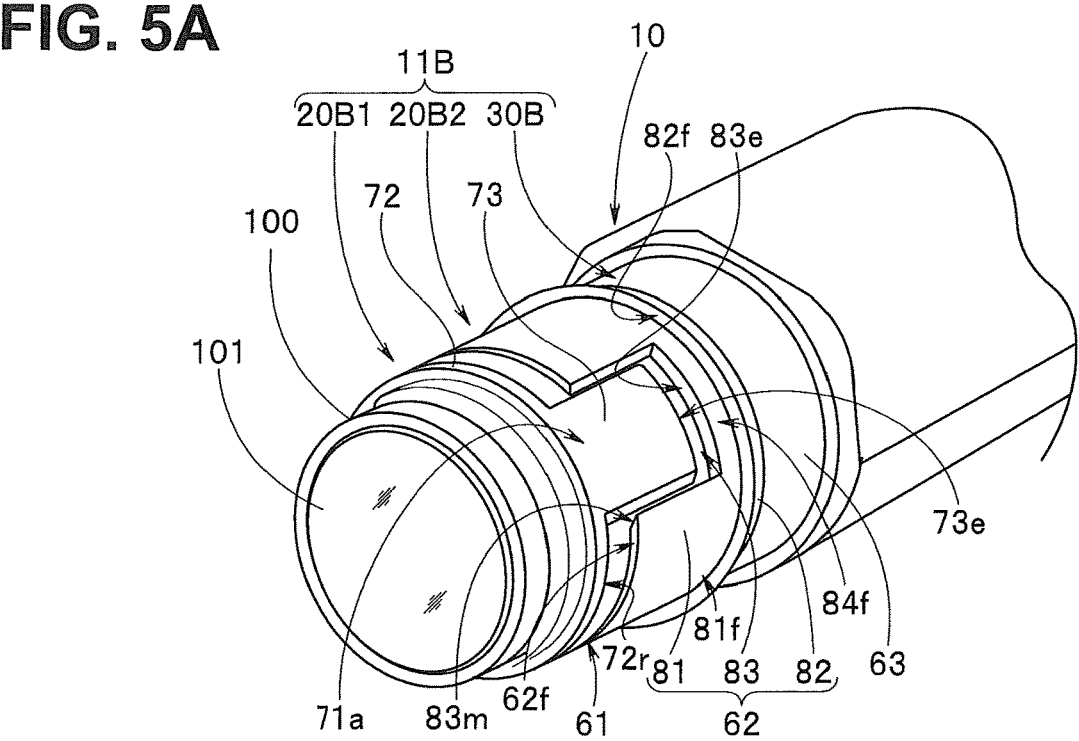
FIG. 5A is a diagram illustrating another configuration example of an optical unit of an image pickup apparatus.
Figure 5B:
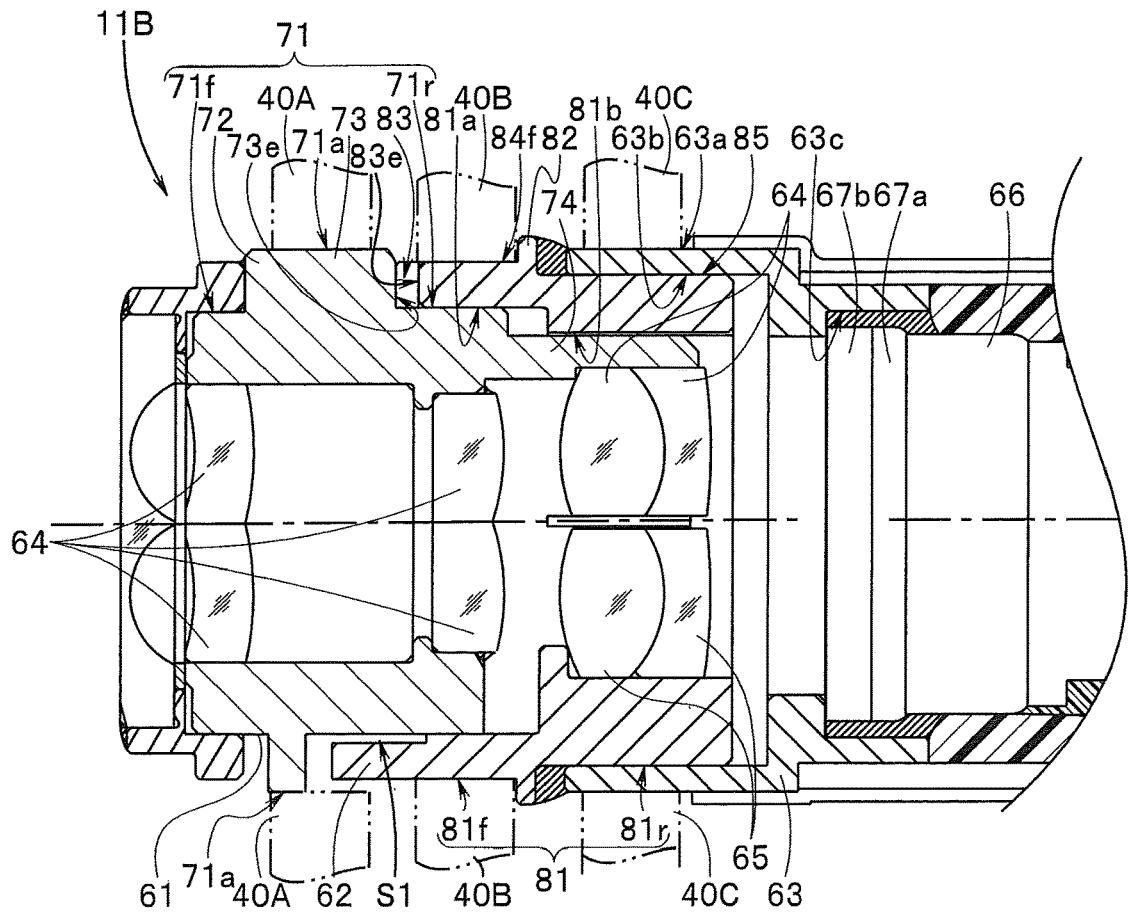
FIG. 5B is a longitudinal sectional view illustrating the optical unit of FIG. 5A and is a diagram illustrating a configuration in which, without increasing lengths of frame members, an objective lens unit jig grasping face is further provided in addition to an outer circumferential face of a projecting portion.
Figure 5C:
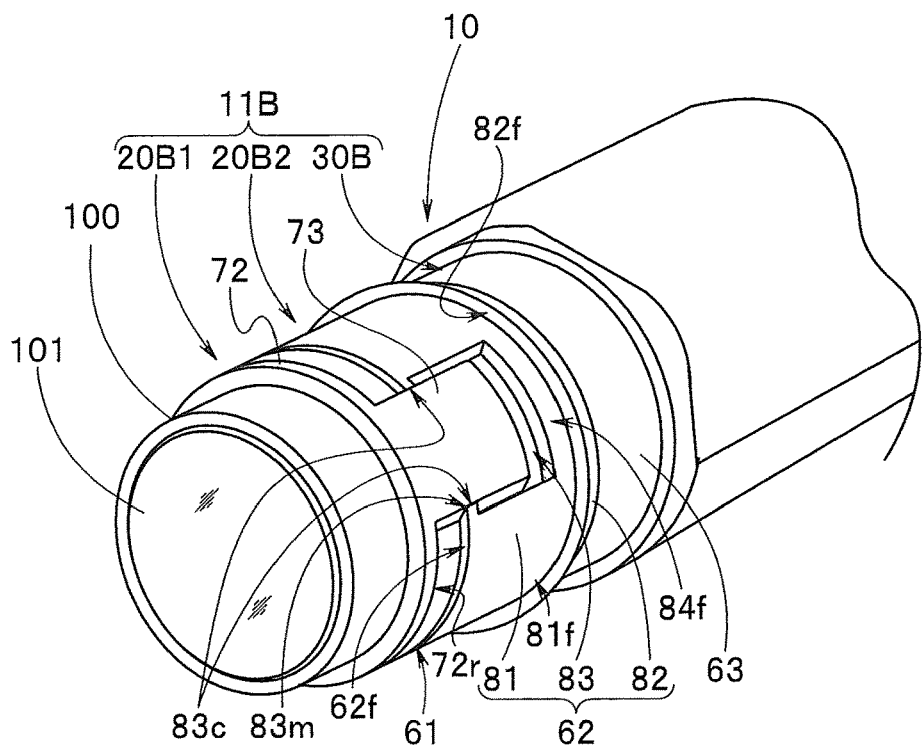
FIG. 5C is a diagram illustrating a relationship between a notch provided with restricting portions at an opening portion of the notch and a holding portion.

An optical unit 11B of the image pickup apparatus 10 shown in FIGS. 5A and 5B is provided with a first objective lens unit 20B1 which is a first optical system, a second objective lens unit 20B2 which is a second optical system and an image pickup unit 30B which is a third optical system.

Reference symbol 100 indicates a distal end frame, and reference symbol 101 indicates a distal end lens. The distal end frame 100 in which the distal end lens 101 is disposed is integrally fixed to a distal end side of a first optical frame 61.

The first objective lens unit 20B1 shown in FIGS. 5A and 5B is provided with the first optical frame 61 configured substantially similarly to the optical frame 21, as a first holding frame. The second objective lens unit 20B2 is provided with a second optical frame 62 configured substantially similarly to the image pickup device frame 31, as a second holding frame. The image pickup unit 30B is provided with an image pickup device frame 63 which is a third holding frame.

As shown in FIG. 5B, the first optical frame 61 is provided with a plurality of optical lenses 64 and the like.

The second optical frame 62 is provided with a plurality of optical lenses 65 and the like. The image pickup device frame 63 is provided with an image pickup device 66, cover lenses 67a and 67b and the like.

As shown in FIGS. 5A and 5B, the first optical frame 61 is provided with a frame body 71 to be a first area, and a projecting portion 72 and a holding portion 73 to be a second area, the first and second areas being substantially similar to the first and second areas of the optical frame 21 described above. A distal-end-side outer circumferential face 71f is provided on a distal end side of the frame body 71 with respect to the projecting portion 72, and a proximal-end-side outer circumferential face 71r is provided on a proximal end side with respect to the projecting portion 72. The proximal-end-side outer circumferential face 71r is a first mating face to mate with a distal-end-side inner circumferential face 81a of the second optical frame 62.

Note that reference symbol 81b indicates a proximal-end-side inner circumferential face. On the proximal-end-side inner circumferential face 81b, an outer circumferential face of a frame body proximal end portion (reference symbol 74 in FIG. 5B) constituting the most proximal end side of the frame body 71 of the first optical frame 61 is to be arranged, being loosely mated with the proximal-end-side inner circumferential face 81b.

The projecting portion 72 is an annular-shaped projecting portion with a predetermined width dimension, the projecting portion 72 projecting from the outer circumferential face of the frame body 71. An outer circumferential face of the projecting portion 72 constitutes a second area outer circumferential face 71a which can be at least the objective lens unit jig grasping face.

The holding portion 73 is an engaging portion projecting from the proximal-end-side outer circumferential face 71r by a predetermined amount and is formed projecting to the proximal end side along the longitudinal axis from a proximal end face 72r side of the projecting portion 72. For example, as shown in FIG. 3C described above, three holding portions 73 are provided in the circumferential direction.

Outer circumferential faces of the holding portions 73 constitute the second area outer circumferential face 71a which can be a first jig grasping face. In other words, in the present embodiment, the outer circumferential faces of the holding portions 73 and the outer circumferential face of the projecting portion 72 constitute the second area outer circumferential face 71a and can constitute the first jig grasping face.

Note that width and length dimensions of the holding portions 73 are set so that such an area that, in consideration of an area of the outer circumferential face of the projecting portion 72, makes it possible to certainly and stably grasp the second area outer circumferential face 71a by the first jig 40A is obtained.

The second optical frame 62 is provided with a frame body 81, a frame body projecting portion 82 and notches 83. The frame body 81 has a frame body distal-end-side outer circumferential face 81f located on a distal end side with respect to the frame body projecting portion 82 and a frame body proximal-end-side outer circumferential face 81r located on a proximal end side with respect to the frame body projecting portion 82.

The frame body distal-end-side inner circumferential face 81a is a second mating face with which the proximal-end-side outer circumferential face 71r of the first optical frame 61 is to be internally mated. A proximal-end-side outer circumferential face 85 is a mating face to mate with a distal-end-side inner circumferential face 63b of the image pickup device frame 63.

A part of the frame body distal-end-side outer circumferential face 81f is a third area 84f which can be a second jig grasping face. The notches 83 are provided on the distal end side of the frame body distal-end-side outer circumferential face 81f. The third area 84f is provided between proximal end faces 83e of the notches 83 and a distal end face 82f of the frame body projecting portion 82 and is grasped by the second jig 40B indicated by a two-dot chain line. Therefore, the third area 84f is set longer than a length of the second jig 40B in the longitudinal direction.

The notches 83 are accommodating portions configured to accommodate the holding portions 73, and three notches 83 are provided in the circumferential direction. The notches 83 have opening portions 83m as openings, on a second optical frame distal end face 62f facing a projecting portion proximal end face 72r of the first optical frame 61.

The holding portions 73 pass through the opening portions 83m, and are accommodated and arranged in the notches 83. Therefore, each of the notches 83 is formed along the longitudinal axis. A width of the notches 83 including a width of the opening portions 83m is set larger than the width of the holding portions 73. Therefore, between inner walls of the notches 83 and side faces of the holding portions 73, there are clearances where adhesive pools are provided.

Note that a relationship between the length of the holding portions 73 in the longitudinal axis direction and a cut depth of the notches 83 in the longitudinal axis direction is set to one of the following two. In one setting, the second optical frame distal end face 62f comes into contact with the projecting portion proximal end face 72r before proximal end faces 83e of the notches 83 come into contact with proximal end faces 73e of the holding portions 73 arranged in the notches 83. In the other setting, the proximal end faces 73e come into contact with the proximal end faces 83e, respectively, before the second optical frame distal end face 62f comes into contact with the projecting portion proximal end face 72r.

Then, in the present embodiment, in a state in which the proximal-end-side outer circumferential face 71r of the first optical frame 61 is mated with the inner circumferential face 81a of the frame body 81, and the holding portions 73 are arranged in the notches 83, the outer circumferential face of the projecting portion 72 and the outer circumferential faces of the holding portions 73, which constitute the second area outer circumferential face 71a, project from the frame body distal-end-side outer circumferential face 81f by a predetermined dimension. In other words, an outer diameter of the second area outer circumferential face 71a is set larger than an outer diameter of the frame body distal-end-side outer circumferential face 81f.

Note that the frame body distal-end-side inner circumferential face 81a may be provided with a gap forming portion for forming the gap S1 described above as necessary. In the present embodiment, the frame body distal-end-side inner circumferential face 81a is provided with the gap S1.

On the image pickup device frame 63, reference symbol 63a indicates a fourth area which can be an image pickup unit jig grasping face (hereinafter referred to as a third jig grasping face). Reference symbol 63b indicates the distal-end-side inner circumferential face, and reference symbol 63c indicates a proximal-end-side inner circumferential face. The proximal-end-side outer circumferential face 85 is internally mated inside the distal-end-side inner circumferential face 63b. The fourth area 63a is grasped by a third jig 40C indicated by a two-dot chain line. Therefore, the fourth area 63a is set longer than a length of the third jig 40C in the longitudinal direction.

Here, assembly between the first optical frame 61 and the second optical frame 62 will be described.

As described above, the worker grasps the second area outer circumferential face 71a, which is the outer circumferential faces of the projecting portion 72 and the holding portions 73 of the first optical frame 61, with the first jig 40A, and grasps the third area 84f of the second optical frame 62 with the second jig 40B.

The worker applies adhesive (not shown) to the proximal-end-side outer circumferential face 71r beforehand and gradually brings the jigs 40A and 40B close to each other. Then, since the gap S1 is provided, a proximal end side portion of the first optical frame 61 is inserted into the second optical frame 62 in a loosely mated state. Then, by the worker further bringing the jigs 40A and 40B close to each other, the proximal end side of the proximal-end-side outer circumferential face 71r of the first optical frame 61 is smoothly fitted inside the inner circumferential face 81a of the frame body 81.

After that, by the proximal-end-side outer circumferential face 71r being fitted inside the inner circumferential face 81a, the proximal-end-side outer circumferential face 71r of the first optical frame 61 and the inner circumferential face 81a of the frame body 81 of the second optical frame 62 are in a mated state with a sufficient bond strength. As described above, adhesive is applied between the mating parts and filled in the gap S1. The proximal end face 73e sides of the holding portions 73 enter the notches 83 from the opening portions 83m, and the holding portions 73 are accommodated into the notches 83.

Then, by the adhesive between the proximal-end-side outer circumferential face 71r and the circumferential face 81a, the adhesive filled in the gap S1 and the adhesive pools in the clearances being cured in this mated state, the first optical frame 61 and the second optical frame 62 are firmly and integrally fixed. Thereby, left and right field-of-view adjustment is completed.

Thus, similarly to the embodiments described above, the first optical frame 61 is provided with the holding portions 73, and the second optical frame 62 is provided with the notches 83 configured to accommodate the holding portions 73. The outer circumferential faces of the holding portions 73 and the outer circumferential face of the projecting portion 72 are made the second area outer circumferential face 71a. An outer diameter of the second area outer circumferential face 71a is set larger than an outer diameter of the frame body distal-end-side outer circumferential face 81f.

Thereby, it is possible to, without increasing a length of the first optical frame 61 and a length of the second optical frame 62, obtain the second area outer circumferential face 71a configured to have such an area that the first jig grasping face, which is a range grasped by the first jig 40A, can be stably grasped by the outer circumferential faces of the holding portions 73 in addition to the outer circumferential face of the projecting portion 72.

As a result, the second area outer circumferential face 71a of the first optical frame 61 can be easily and certainly grasped by the first jig 40A.

Further, the outer diameter of the second area outer circumferential face 71a is set larger than the outer diameter of the frame body distal-end-side outer circumferential face 81f. As a result, a problem of the first jig 40A coming into contact with the second optical frame 62 when grasping the second area outer circumferential face 71a can be solved.

By certainly grasping the first optical frame 61 with the first jig 40A, certainly grasping the second optical frame 62 with the second jig 40B, and stably performing change of the mating length at the time of assembly, stereoscopic field-of-view adjustment is realized.

Other operations and effects are similar to the operations and effects of the embodiments described above.

Note that, at the time of assembling the second optical frame 62 and the image pickup device frame 63, the third area 84f of the second optical frame 62 described above is grasped by the second jig 40B, and the fourth area 63a of the image pickup device frame 63 is grasped by the third jig 40C.

Further, adhesive (not shown) is applied to the frame body proximal-end-side outer circumferential face 81r beforehand. Then, while the jigs 40B and 40C are being gradually brought close to each other, and the frame body proximal-end-side outer circumferential face 81r of the second optical frame 62 is being inserted inside the distal-end-side inner circumferential face 63b of the image pickup device frame 63, focus adjustment is performed.

After that, by the adhesive between the frame body proximal-end-side outer circumferential face 81r and the inner circumferential face 63 being cured, the second optical frame 62 and the image pickup device frame 63 are firmly and integrally fixed, and positioning in the longitudinal direction, that is, focus adjustment is completed.

Note that, in the embodiment described above, the width of the notches 83 each of which is formed along the longitudinal axis direction, including the width of the opening portions 83m, is set larger than the width of the holding portions 73 beforehand to improve assemblability. In a stereoscopic endoscope, however, there is a possibility that, by the first optical frame 61 and the second optical frame 62 rotating around the axis, optical axes of the respective optical systems are displaced from each other, and a problem may occur in a stereoscopic observation image.

Therefore, in the configuration in which the plurality of holding portions 73 and notches 83 are provided, restricting portions 83c are provided on the opening portion 83m side for only one pair of a holding portion 73 and a notch 83 among the plurality of pairs. A width of the restricting portions 83c in the circumferential direction (a rotation direction) is set larger than the width of the holding portions 73 in the circumferential direction by an amount corresponding to a predetermined clearance.

According to the above configuration, positioning of one holding portion 73 can be performed with a high accuracy by the restricting portions 83c. As a result, while the problem that the first optical frame 61 and the second optical frame 62 are displaced around the axis (in the rotation direction) is solved, adjustment in the longitudinal direction can be smoothly performed.

It is preferable that a face shape of a part where each restricting portion 83c comes into contact with the side face of the holding portion 73 is a curved face, but the face shape may be a plane.

Figure 6A:
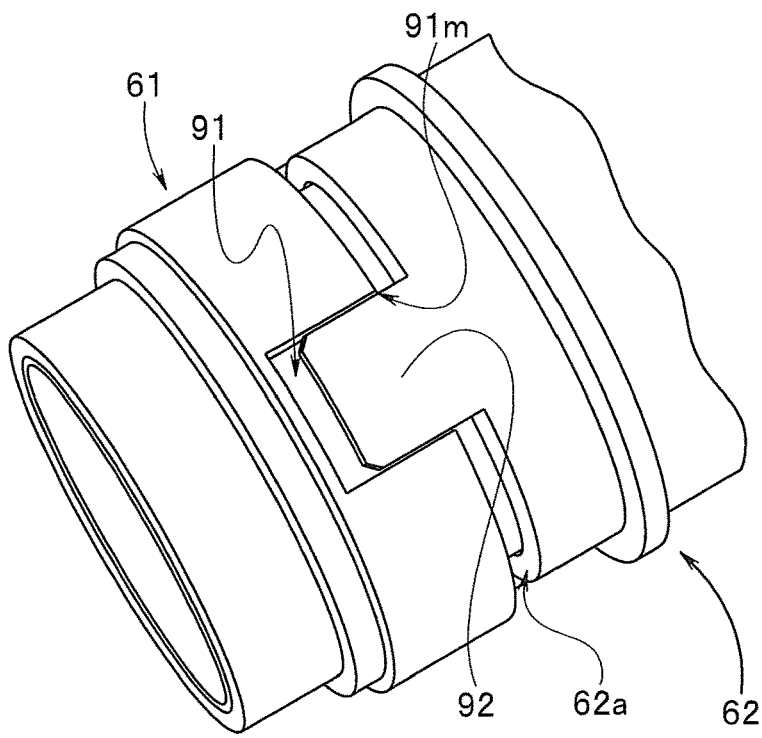
FIG. 6A is a diagram illustrating a relationship between a first optical frame provided with a recess portion on the first optical frame and a second optical frame provided with a nail part.

In the embodiment shown in FIGS. 5A and 5B described above, the first optical frame 61 is provided with the holding portions 73, and the second optical frame 62 is provided with the notches 83. However, the first optical frame 61 may be provided with a recess portion 91, and the second optical frame 62 may be provided with a nail portion 92 projecting from the second optical frame distal end face 62f as shown in FIG. 6A.

In the above configuration, a relationship between the nail portion 92 and the recess portion 91 is similar to the relationship in the configuration shown in FIGS. 4A and 4B described above, and a gap S2 into which adhesive is to be filled may be provided between mating parts of the nail portion 92 and the recess portion 91.

According to the above configuration, since mated portions between the first optical frame 61 and the second optical frame 62 are configured with the proximal-end-side outer circumferential face 71r and the frame body distal-end-side inner circumferential face 81a of the frame body 81, and the nail portions 92 and bottom faces of the recess portions 91, a sufficiently mated state can be obtained.

Then, by adhesive between the proximal-end-side outer circumferential face 71r and the inner circumferential face 81a and adhesive filled in the adhesive filling gaps being cured in the above mated state, the first optical frame 61 and the second optical frame 62 can be firmly and integrally fixed.

Figure 6B:
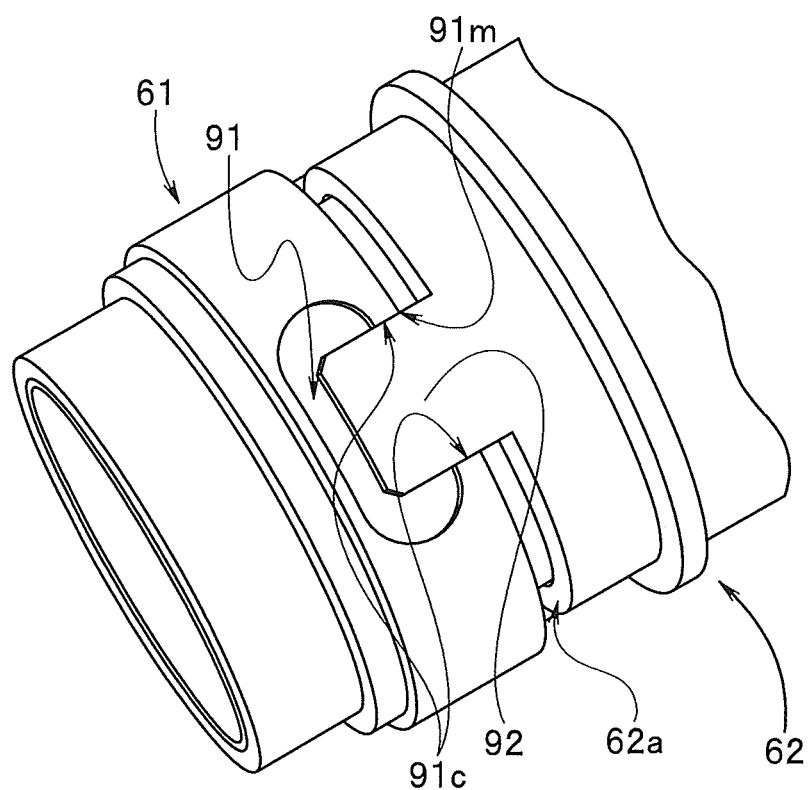
FIG. 6B is a diagram illustrating a relationship between the recess portion provided with restricting portions at an opening portion of the recess portion and the nail portion.

Note that, in the configuration in which the first optical frame 61 is provided with the recess portions 91, and the second optical frame 62 is provided with the plurality of nail portions 92, restricting portions 91c are also provided for only one pair of a recess portion 91 and a nail portion 92, on an opening portion 91m side, the opening portion 91m being an opening of the recess portion 91, as shown in FIG. 6B. A width of the restricting portions 91c is set larger than a width of the nail portions 92 by an amount corresponding to a predetermined clearance.

According to the above configuration, positioning of one nail portion 92 is performed with a high accuracy by the restricting portions 91c, and it is possible to, while preventing the problem of the first optical frame 61 and the second optical frame 62 being relatively displaced around the axis, smoothly perform adjustment in the longitudinal direction.

Note that the present invention is not limited to the embodiments described above, and various modifications can be made within a range not departing from the gist of the invention.

According to the present invention, it is possible to, without increasing lengths of frame members, realize such an optical unit that makes it possible to secure a mating length of a mated portion between frames, easily perform highly accurate focus adjustment, cause resistance to external forces to be improved and perform positioning of a lens in a circumferential direction.

What is claimed is:

1. An optical unit comprising:
a first optical system arranged on a distal end side;
a second optical system that is coaxial with the first optical system and is arranged on a proximal end side of the first optical system;
a first holding frame in which the first optical system is provided;
a second holding frame in which the second optical system is provided;
a first mating face provided on a proximal end side of the first holding frame and forming an outer circumferential face, the first mating face comprising a mated portion between the first holding frame and the second holding frame;
a second mating face provided on an inner circumferential face on a distal end side of the second holding frame, the second mating face being arranged mating with the first mating face;
a plurality of recesses provided apart in a circumferential direction on an outer circumferential face of one of the first holding frame and the second holding frame, the plurality of recesses each having an opening on an end face side where the first holding frame and the second holding frame face each other, the plurality of recesses each having a length formed along the optical axis; and
a plurality of projections provided on an outer circumferential face of an other of the first holding frame and the second holding frame, the plurality of projections each passing through a corresponding opening such that each of the plurality of projections are disposed in a corresponding one of the plurality of recesses, wherein
in a state in which each of the plurality of projections are disposed in the corresponding one of the plurality of recesses, a bottom face of each of the plurality of recesses and a mating face of each corresponding one of the plurality of projections are in a mated state.

2. The optical unit according to claim 1, wherein
the first holding frame includes a first area having a first outer diameter and a second area having a second outer diameter larger than the first outer diameter,
the second area is projected at least from the outer circumferential face of the first holding frame and extends in the circumferential direction, and
an outer diameter of the plurality of projections is smaller than the second outer diameter of the second area.

3. The optical unit according to claim 1, wherein, for one projection of the plurality of projections and one corresponding recess of the plurality of recesses, a clearance in the circumferential direction between the opening of the one accommodating recess and the one corresponding projection is smaller than a clearance in the circumferential direction between the opening of other of the plurality of recesses and corresponding projections.

4. The optical unit according to claim 1, wherein a gap is formed between an end side of each of the projections and a corresponding end side of each of the plurality of recesses and each gap serves as an adhesive pool for adhesive applied between the bottom face and the mating face.

5. An optical unit comprising:
a first optical system;
a second optical system arranged coaxially with the first optical system;
a first holding frame in which the first optical system is provided;
a second holding frame in which the second optical system is provided, the second holding frame mating with the first holding frame;
a first mating face provided on the first holding frame and forming an outer circumferential face, the first mating face comprising a mated portion between the first holding frame and the second holding frame;
a second mating face provided on an inner circumferential face of the second holding frame, the second mating face being arranged mating with the first mating face;
a plurality of recesses provided apart in a circumferential direction on an outer circumferential face of one of the first holding frame and the second holding frame, the plurality of recesses each having an opening on an end face side where the first holding frame and the second holding frame face each other, the plurality of recesses each having a length formed along the optical axis; and
a plurality of projections provided on an outer circumferential face of an other of the first holding frame and the second holding frame, the plurality of projections each passing through a corresponding opening such that each of the plurality of projections are disposed in a corresponding one of the plurality of recesses, wherein in a state in which each of the plurality of projections are disposed in the corresponding one of the plurality of recesses, a bottom face of each of the plurality of recesses and a mating face of each corresponding one of the plurality of projections are in a mated state.

6. The optical unit according to claim 4, wherein each gap and clearances between each of the projections and each of the corresponding projections are filled with the adhesive.

7. The optical unit according to claim 5, wherein a gap is formed between an end side of each of the projections and a corresponding end side of each of the plurality of recesses and each gap serves as an adhesive pool for adhesive applied between the bottom face and the mating face.

8. The optical unit according to claim 1, each of the first and second holding frames have an internal cavity, the first and second optical systems being held in the internal cavity of the first and second holding frames, respectively.

9. The optical unit according to claim 5, each of the first and second holding frames have an internal cavity, the first and second optical systems being held in the internal cavity of the first and second holding frames, respectively.

\* \* \* \* \*